US008718233B2

(12) United States Patent
Yuan

(10) Patent No.: US 8,718,233 B2
(45) Date of Patent: May 6, 2014

(54) LINKAGE MECHANISM, A COLLIMATOR, AND AN X-RAY MACHINE

(75) Inventor: Ping Yuan, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 393 days.

(21) Appl. No.: 13/312,497

(22) Filed: Dec. 6, 2011

(65) Prior Publication Data

US 2012/0148028 A1 Jun. 14, 2012

(30) Foreign Application Priority Data

Dec. 9, 2010 (CN) .......................... 2010 1 0586774

(51) Int. Cl.
*G21K 1/04* (2006.01)
(52) U.S. Cl.
CPC ....................................... *G21K 1/04* (2013.01)
USPC ........................................................ 378/150
(58) Field of Classification Search
CPC ........... G21K 1/04; G21K 1/02; G21K 1/046; A61B 6/06; A61B 6/0306
USPC ......................................... 378/145, 147–155
See application file for complete search history.

(56) References Cited

U.S. PATENT DOCUMENTS

| 4,246,288 | A | | 1/1981 | Sanborn, Jr. |
| 5,291,539 | A | * | 3/1994 | Thumann et al. ............. 378/154 |
| 6,389,108 | B1 | * | 5/2002 | Ein-Gal ......................... 378/147 |
| 7,260,183 | B2 | | 8/2007 | Yuan et al. |
| 7,672,435 | B2 | * | 3/2010 | Hashimoto ................... 378/148 |
| 7,680,249 | B2 | | 3/2010 | Yuan |
| 2010/0054420 | A1 | | 3/2010 | Yuan |
| 2010/0189216 | A1 | | 7/2010 | Yuan |
| 2010/0246775 | A1 | | 9/2010 | Yuan |
| 2010/0260318 | A1 | | 10/2010 | Yuan |
| 2012/0043481 | A1 | * | 2/2012 | Mansfield et al. ......... 250/492.1 |

* cited by examiner

*Primary Examiner* — Irakli Kiknadze
(74) *Attorney, Agent, or Firm* — Armstrong Teasdale LLP

(57) ABSTRACT

A linkage mechanism of a scattered ray inhibition apparatus and a radiation field control apparatus is provided. The linkage mechanism includes a first timing belt, a second timing belt, and a transmission mechanism between the first timing belt and the second timing belt, wherein the scattered ray inhibition apparatus is mounted on the first timing belt, the radiation field control apparatus is mounted on the second timing belt, the transmission ratio of the transmission mechanism is equal to the ratio of the moving speed of the scattered ray inhibition apparatus to the moving speed of the radiation field control apparatus.

20 Claims, 3 Drawing Sheets

LINKAGE MECHANISM, A COLLIMATOR, AND AN X-RAY MACHINE

CROSS REFERENCE TO RELATED APPLICATIONS

This application claims the benefit of Chinese Patent Application No. 201010586774.9 filed Dec. 9, 2010, which is hereby incorporated by reference in its entirety.

BACKGROUND OF THE INVENTION

The invention generally relates to the field of an X-ray machine, and in particular relates to a linkage mechanism of a scattered ray inhibition apparatus and a radiation field control apparatus, a collimator, and an X-ray machine.

In the field of the X-ray machine, a radiation field control apparatus exists in a collimator for limiting the X-ray Field of View (FOV) of X-rays emitted from a tube, and it is generally composed of two rectangular blades that are oppositely disposed. As is well-known, there is a certain distance between the tube and the collimator, thus a part of the X-rays emitted from the tube will be scattered from the distance, which also may be called off-focal radiation. For a general X-ray machine, the amount of the off-focal radiation thereof normally approaches 15% of the amount of the focal radiation. In addition to the primary X-ray beams, the part of off-focal radiation also will radiate on a patient, which thus increases X-ray dosage to the patient and also affects the quality of imaging, and also makes faint images of the anatomical structures outside the field of interest.

Therefore, in order to solve the problem, a scattered ray inhibition apparatus is generally disposed over the distance between the tube and the collimator for inhibiting the X-rays emitted from the tube from being scattered from the distance. The scattered ray inhibition apparatus usually employs a fixed blade disposed in a plane which is as close as possible to the exit of the tube, or a fixed cone. For an X-ray machine, the tube emits cone-shaped X-ray beams, when the FOV changes, the scattered ray inhibition apparatus remains unchanged, thus, in the case of a small FOV, the quality of imaging is rather undesirable. Hence, the scattered ray inhibition apparatus needs to be in linkage with the radiation field control apparatus.

At present, at least some known X-ray machines have had the function of linking the scattered ray inhibition apparatus with the radiation field control apparatus. However, they generally have a wheel disc and a shift lever mounted between the scattered ray inhibition apparatus and the radiation field control Apparatus. One end of the shift lever is connected to the radiation field control apparatus while the other end thereof is connected to one end of the wheel disc, and the other end of the wheel disc is connected to one end of the blade (the scattered ray inhibition apparatus). Thus, as the radiation field control apparatus changes, the shift lever drives the wheel disc, the wheel disc further drives the blade, causing the blade to swing. Hence, the inhibition effect in such manner is undesirable and the structure is comparatively complicated. Since the tube of the X-ray machine emits cone-shaped radiation beams, if the blade or the cone is able to translate with the motion of the radiation field control apparatus, the achieved inhibition effect is then ideal.

U.S. Pat. No. 4,246,288 also discloses a method of linking a scattered ray inhibition apparatus with a radiation field control apparatus, but the method is complicated in structure.

SUMMARY OF THE INVENTION

The embodiments described herein provide a linkage mechanism of a scattered ray inhibition apparatus and an radiation field control apparatus, a collimator, and an X-ray machine that may reduce influence of off-focal radiation upon a patient.

The linkage mechanism of the scattered ray inhibition apparatus and the radiation field control apparatus described herein includes a first timing belt, a second timing belt and a transmission mechanism between the first timing belt and the second timing belt, wherein, the scattered ray inhibition apparatus is mounted on the first timing belt, the radiation field control apparatus is mounted on the second timing belt, the transmission ratio of the transmission mechanism is equal to the ratio of the moving speed of the scattered ray inhibition apparatus to the moving speed of the radiation field control apparatus.

In one embodiment, the transmission mechanism comprises at least two gears.

In one embodiment, the transmission mechanism further includes a third timing belt connected to the first timing belt and a fourth timing belt connected to the second timing belt, wherein the at least two gears are disposed between the third timing belt and the fourth timing belt.

In one embodiment, the linkage mechanism of the scattered ray inhibition apparatus and the radiation field control apparatus further includes a first linear guideway, the scattered ray inhibition apparatus is connected to the first timing belt through the first linear guideway.

Further, the linkage mechanism of the scattered ray inhibition apparatus and the radiation field control apparatus further includes a second linear guideway, the radiation field control apparatus is connected to the second timing belt through the second linear guideway.

Further, the linkage mechanism of the scattered ray inhibition apparatus and the radiation field control apparatus further includes an electrical motor for supplying power to the transmission mechanism.

In another aspect, the collimator of the includes a linkage mechanism of a scattered ray inhibition apparatus and a radiation field control apparatus, the linkage mechanism includes a first timing belt, a second timing belt and a transmission mechanism between the first timing belt and the second timing belt, wherein the scattered ray inhibition apparatus is mounted on the first timing belt, the radiation field control apparatus is mounted on the second timing belt, the transmission ratio of the transmission mechanism is equal to the ratio of the moving speed of the scattered ray inhibition apparatus to the moving speed of the radiation field control apparatus.

In one embodiment, the transmission mechanism includes at least two gears.

In one embodiment, the transmission mechanism further includes a third timing belt connected to the first timing belt and a fourth timing belt connected to the second timing belt, wherein, the at least two gears are disposed between the third timing belt and the fourth timing belt.

Further, in one embodiment, the transmission mechanism further includes a first linear guideway, and the scattered ray inhibition apparatus is connected to the first timing belt through the first linear guideway.

Further, in one embodiment, the transmission mechanism further includes a second linear guideway, the radiation field control apparatus is connected to the second timing belt through the second linear guideway.

In another aspect, an X-ray machine includes a linkage mechanism of a scattered ray inhibition apparatus and a radiation field control apparatus, the linkage mechanism includes a first timing belt, a second timing belt and a transmission mechanism between the first timing belt and the second timing belt, wherein the scattered ray inhibition apparatus is mounted on the first timing belt, the radiation field control apparatus is mounted on the second timing belt, the transmission ratio of the transmission mechanism is equal to the ratio of the moving speed of the scattered ray inhibition apparatus to the moving speed of the radiation field control apparatus.

In one embodiment, the transmission mechanism includes at least two gears.

In one embodiment, the transmission mechanism further includes a third timing belt connected to the first timing belt and a fourth timing belt connected to the second timing belt, wherein the at least two gears are disposed between the third timing belt and the fourth timing belt.

Further, the transmission mechanism further includes a first linear guideway, the scattered ray inhibition apparatus is connected to the first timing belt through the first linear guideway.

Further, the transmission mechanism further includes a second linear guideway, the radiation field control apparatus is connected to the second timing belt through the second linear guideway.

Compared to the prior art, the linkage mechanism of the scattered ray inhibition apparatus and the radiation field control apparatus and the X-ray machine have several advantages.

Since the embodiments described herein include a scattered ray inhibition apparatus mounted on the first timing belt, the scattered ray inhibition apparatus may translate, which thus may ensure a reduction of influence of off-focal radiation upon human bodies.

Since the transmission ratio of the transmission mechanism is equal to the ratio of the moving speed of the scattered ray inhibition apparatus to the moving speed of the radiation field control apparatus, as such, it may ensure the linkage of the scattered ray inhibition apparatus with the radiation field control apparatus.

Moreover, the structure of the embodiments described herein is simple, reliable and easy to realize.

BRIEF DESCRIPTION OF THE DRAWINGS

In order to more thoroughly understand the embodiments described herein, reference is made to the description in conjunction with the following Figures.

DETAILED DESCRIPTION OF THE INVENTION

Specific embodiments will be described in detail below, however, the invention is not limited to the following specific embodiments stated.

Figure 1:
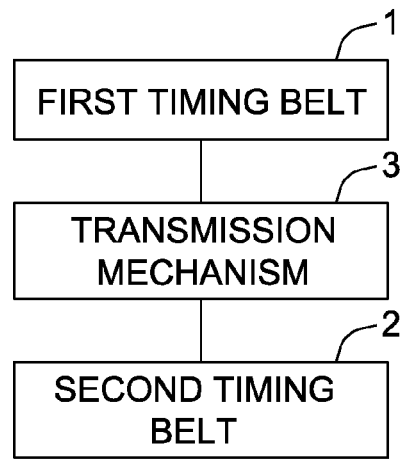
FIG. 1 illustrates a schematic diagram of an exemplary linkage mechanism of a scattered ray inhibition apparatus and a radiation field control apparatus.

As shown in FIG. 1, a linkage mechanism of a scattered ray inhibition apparatus and a radiation field control apparatus includes a first timing belt 1, a second timing belt 2 and a transmission mechanism 3 between the first timing belt 1 and the second timing belt 2, wherein the scattered ray inhibition apparatus 10 (see FIG. 2) is mounted on the first timing belt 1, the radiation field control apparatus 11 (see FIG. 2) is mounted on the second timing belt 2, the transmission ratio of the transmission mechanism 3 is equal to the ratio of the moving speed of the scattered ray inhibition apparatus 10 to the moving speed of the radiation field control apparatus 11.

Figure 3:
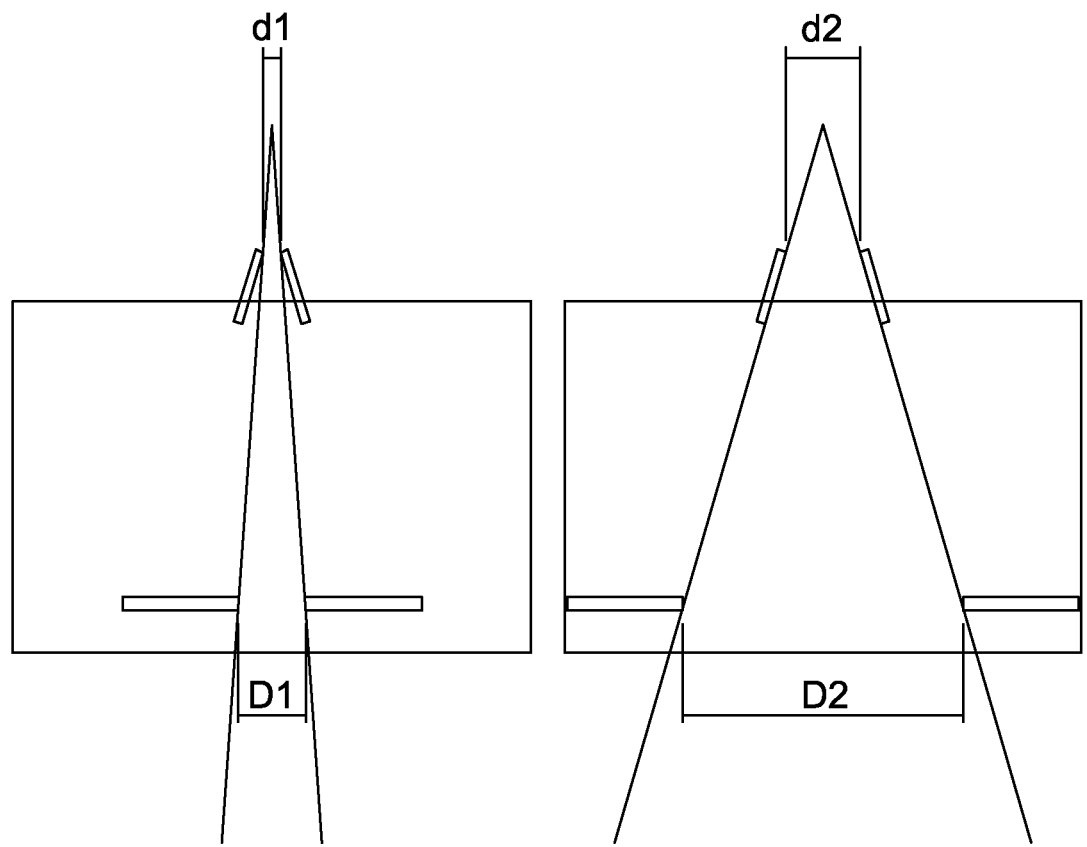
FIG. 3 illustrates a schematic diagram of the relation of speed between the scattered ray inhibition apparatus and the radiation field control apparatus shown in FIG. 1.

When the FOV changes, that is, when the radiation field control apparatus 11 moves, the scattered ray inhibition apparatus 10 also should move, thus linkage may be realized. For a particular X-ray machine, the ratio of the moving speed of the scattered ray inhibition apparatus 10 to the moving speed of the radiation field control apparatus 11 is determined. As shown in FIG. 3, it illustrates a schematic diagram of the relation of speed between the scattered ray inhibition apparatus and the radiation field control apparatus.

Since $V0=((d2-d1)/2)/T$; $V2=((D2-D1)/2)/T$;

wherein, V0 indicates the moving speed of the scattered ray inhibition apparatus 10, V2 indicates the moving speed of the radiation field control apparatus, T indicates the moving time for the scattered ray inhibition apparatus 10 and the radiation field control apparatus 11 to move from the largest opening to the smallest opening, d1 indicates the minimum distance between the two blades when the scattered ray inhibition apparatus has the smallest opening, d2 indicates the minimum distance between the two blades when the scattered ray inhibition apparatus has the largest opening, D1 indicates the minimum distance between the two blades when the radiation field control apparatus has the smallest opening, D2 indicates the minimum distance between the two blades when the radiation field control apparatus has the largest opening.

Therefore the ratio may be obtained through the following formula:

$$V_0/V_2=(d2-d1)/(D2-D1)$$

Figure 2:
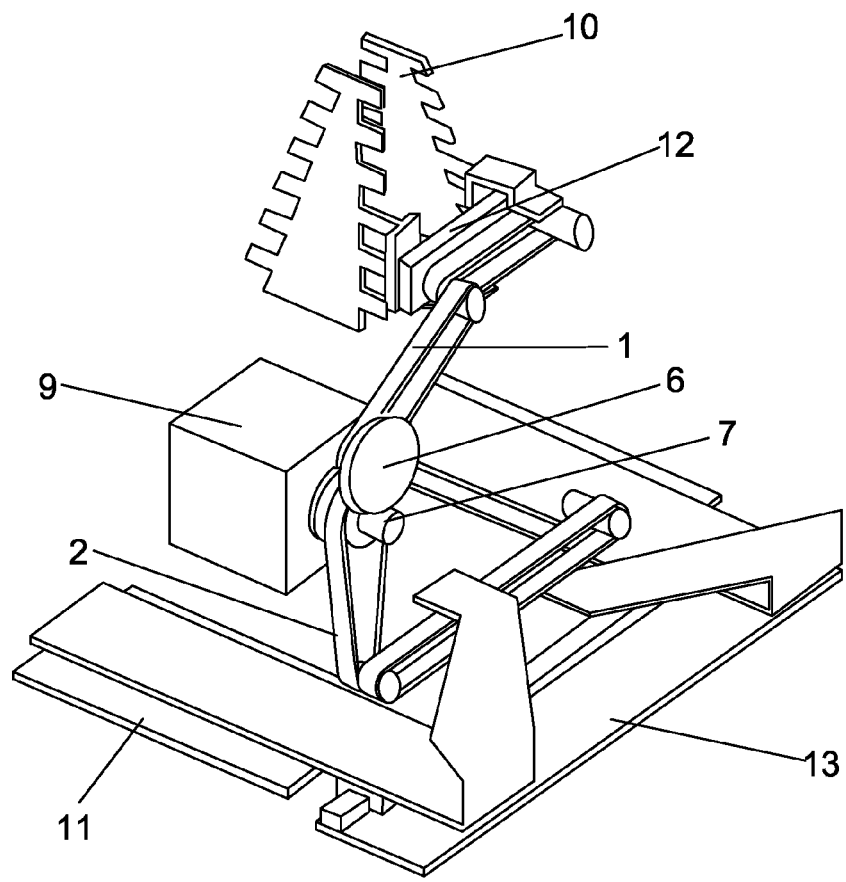
FIG. 2 illustrates a schematic diagram of one embodiment of a linkage mechanism of a scattered ray inhibition apparatus and a radiation field control apparatus.

As shown in FIG. 2, the linkage mechanism further may include a first linear guideway 12, the scattered ray inhibition apparatus 10 is connected to the first timing belt 1 through the first linear guideway 12.

Additionally, the linkage mechanism further may include a second linear guideway 13, the radiation field control apparatus 11 is connected to the second timing belt 2 through the second linear guideway 13.

Again as shown in FIG. 2, the linkage mechanism further may include an electrical motor 9 for supplying power to the transmission mechanism 3. The electrical motor 9 may be mounted on the gear shaft of gear 7 and gear 6 (see FIG. 2), and also may be mounted in positions of other gears or timing belt pulleys.

As for the transmission mechanism 3, it may be designed in any method that has been known or may be known by those skilled in the art in the future, as long as the transmission ratio of the transmission mechanism 3 is equal to the ratio of the moving speed of the scattered ray inhibition apparatus 10 to the moving speed of the radiation field control apparatus 11.

For example, the transmission mechanism 3 may only include two gears, the transmission ratio of the two gears is the ratio of the moving speed of the scattered ray inhibition apparatus 10 to the moving speed of the radiation field control apparatus 11. Of course, the transmission mechanism 3 also may include more than two gears.

Figure 4:
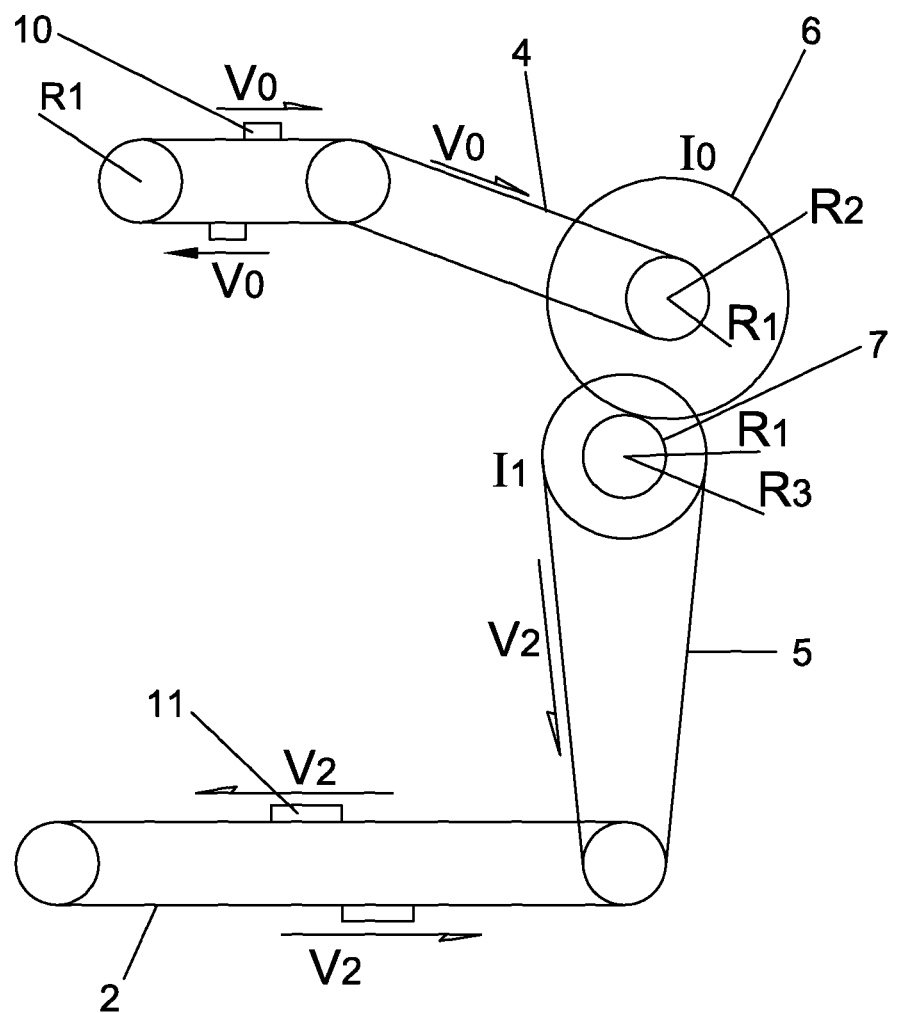
FIG. 4 illustrates a schematic diagram of one embodiment of a linkage mechanism of a scattered ray inhibition apparatus and a radiation field control apparatus.

FIG. 4 illustrates a schematic diagram of one embodiment of a linkage mechanism of a scattered ray inhibition apparatus and a radiation field control apparatus. The transmission mechanism 3 may include a third timing belt 4 connected to the first timing belt 1, a fourth timing belt 5 connected to the second timing belt 2, and a first gear 6 and a second gear 7 disposed between the third timing belt 4 and the fourth timing belt 5 for implementing transmission.

In the example, the radiuses of timing belt pulleys of the first timing belt 1, the second timing belt 2 and the third timing belt 4 are all set to be R1, the radius of one timing belt pulley of the fourth timing belt 5 is R1, and the radius of the other timing belt pulley thereof is R3, and the radius of the first gear 6 is set to be R2, the radius of the second gear 7 is set to be R1, V0 indicates the moving speed of the scattered ray inhibition apparatus 10, V2 indicates the moving speed of the radiation field control apparatus 11, I0 indicates the transmission ratio of the electrical motor 9 to the second gear 7, I1 indicates the transmission ratio of the larger pulley of the fourth timing belt 5 to the timing belt pulley of the third timing belt 4, wherein, $$I_0 = R2/R1$$

$$I_1 = R3/R1$$

$$V_2 = I_0 * I_1 * V_0 = ((R2*R3)/(R1*R1)) * V_0$$

$$V_2/V_0 = (R2*R3)/(R1*R1)$$

For a particular X-ray machine, V2/V0 is constant. As for this embodiment, the value thereof is 6, thus, $$(R2*R3)/(R1*R1) = 6 \qquad (1)$$

Therefore, in one example, for the values of R1, R2 and R3 satisfy the formula (I), e.g., R1 is 7, R2 is 21, R3 is 14 (length unit).

In another aspect, collimator is provided that includes a linkage mechanism of a scattered ray inhibition apparatus and a radiation field control apparatus, the linkage mechanism including a first timing belt 1, a second timing belt 2 and a transmission mechanism 3 between the first timing belt 1 and the second timing belt 2, wherein the scattered ray inhibition apparatus 10 is mounted on the first timing belt 1, the radiation field control apparatus 11 is mounted on the second timing belt 2, the transmission ratio of the transmission mechanism 3 is equal to the ratio of the moving speed of the scattered ray inhibition apparatus 10 to the moving speed of the radiation field control apparatus 11.

In one embodiment, the transmission mechanism 3 includes at least two gears, the total transmission ratio between the gears is the ratio of the moving speed of the scattered ray inhibition apparatus 10 to the moving speed of the radiation field control apparatus 11.

According to one embodiment, the transmission mechanism 3 may include a third timing belt 4 connected to the first timing belt 1, a fourth timing belt 5 connected to the second timing belt 2 and at least two gears between the third timing belt 4 and the fourth timing belt 5 for implementing transmission.

Again as shown in FIG. 2, the transmission mechanism 3 of the collimator further includes a first linear guideway 12, the scattered ray inhibition apparatus 10 is connected to the first timing belt 1 through the first linear guideway 12.

Further, the transmission mechanism 3 of the collimator further includes a second linear guideway 13, the radiation field control apparatus 11 is connected to the second timing belt 2 through the second linear guideway 13.

In addition, the transmission mechanism 3 of the collimator further includes an electrical motor 9 for supplying power to the transmission mechanism 3.

An X-ray machine is provided, which includes a linkage mechanism of a scattered ray inhibition apparatus and a radiation field control apparatus, the linkage mechanism includes a first timing belt 1, a second timing belt 2 and a transmission mechanism 3 between the first timing belt 1 and the second timing belt 2, wherein the scattered ray inhibition apparatus 10 is mounted on the first timing belt 1, the radiation field control apparatus 11 is mounted on the second timing belt 2, the transmission ratio of the transmission mechanism 3 is equal to the ratio of the moving speed of the scattered ray inhibition apparatus 10 to the moving speed of the radiation field control apparatus 11.

In one example, the transmission mechanism 3 may include two gears, the ratio of diameters of the two gears is the ratio of the moving speed of the scattered ray inhibition apparatus 10 to the moving speed of the radiation field control apparatus 11.

In another example, the transmission mechanism 3 includes a third timing belt 4 connected to the first timing belt 1, a fourth timing belt 5 connected to the second timing belt 2, and a first gear 6 and a second gear 7 disposed between the third timing belt 4 and the fourth timing belt 5 for implementing transmission.

In one embodiment, the X-ray machine further includes a first linear guideway 12, the scattered ray inhibition apparatus 10 is connected to the first timing belt 1 through the first linear guideway 12.

Further, the X-ray machine further may include a second linear guideway 13, the radiation field control apparatus 11 is connected to the second timing belt 2 through the second linear guideway 13.

In addition, the X-ray machine further includes an electrical motor 9 for supplying power to the transmission mechanism 3.

Because the linkage mechanism in the collimator and the linkage mechanism in the X-ray machine described herein are similar to the linkage mechanism of a scattered ray inhibition apparatus and a radiation field control apparatus described herein, the linkage mechanism in the collimator and the linkage mechanism in the X-ray machine will not be described in detail herein.

Although the embodiments of the present invention are described as above in combination with the figures, those skilled in the art may implement various variation, modification and equivalent substitution to the invention without departing from the spirit and scope of the present invention. Such variation, modification and equivalent substitution are all intended to fall within the spirit and scope defined by the appended claims.

What is claimed is:

1. A linkage mechanism of a scattered ray inhibition apparatus and a radiation field control apparatus, said linkage mechanism comprising:
   a first timing belt;
   a second timing belt; and
   a transmission mechanism between said first timing belt and said second timing belt, wherein said scattered ray inhibition apparatus is mounted on said first timing belt, said radiation field control apparatus is mounted on said second timing belt, the transmission ratio of said transmission mechanism is equal to the ratio of the moving speed of said scattered ray inhibition apparatus to the moving speed of said radiation field control apparatus.

2. The linkage mechanism according to claim 1, wherein said transmission mechanism comprises at least two gears.

3. The linkage mechanism according to claim 2, wherein said transmission mechanism further comprises:
   a third timing belt connected to said first timing belt; and
   a fourth timing belt connected to said second timing belt, wherein said at least two gears are disposed between said third timing belt and said fourth timing belt.

4. The linkage mechanism according to claim 1 further comprising a first linear guideway, said scattered ray inhibition apparatus connected to said first timing belt through said first linear guideway.

5. The linkage mechanism according to claim 4 further comprising a second linear guideway, said radiation field control apparatus connected to said second timing belt through said second linear guideway.

6. The linkage mechanism according to claim 5 further comprising an electrical motor configured to supply power to said transmission mechanism.

7. The linkage mechanism according to claim 1 further comprising a second linear guideway, said radiation field control apparatus connected to said second timing belt through said second linear guideway.

8. The linkage mechanism according to claim 7 further comprising an electrical motor configured to supply power to said transmission mechanism.

9. A collimator comprising a linkage mechanism of a scattered ray inhibition apparatus and a radiation field control apparatus, wherein said linkage mechanism comprises:
a first timing belt;
a second timing belt; and
a transmission mechanism between said first timing belt and said second timing belt, wherein said scattered ray inhibition apparatus is mounted on said first timing belt, said radiation field control apparatus is mounted on said second timing belt, the transmission ratio of said transmission mechanism is equal to the ratio of the moving speed of said scattered ray inhibition apparatus to the moving speed of said radiation field control apparatus.

10. The collimator according to claim 9, wherein said transmission mechanism comprises at least two gears.

11. The collimator according to claim 10, wherein said transmission mechanism further comprises:
a third timing belt connected to said first timing belt; and
a fourth timing belt connected to said second timing belt, wherein said at least two gears are disposed between said third timing belt and said fourth timing belt.

12. The collimator according to claim 9 further comprising a first linear guideway, said scattered ray inhibition apparatus being connected to said first timing belt through said first linear guideway.

13. The collimator according to claim 12 further comprising a second linear guideway, said radiation field control apparatus being connected to said second timing belt through said second linear guideway.

14. The collimator according to claim 9 further comprising a second linear guideway, said radiation field control apparatus being connected to said second timing belt through said second linear guideway.

15. An X-ray machine comprising a linkage mechanism of a scattered ray inhibition apparatus and a radiation field control apparatus, said linkage mechanism comprising:
a first timing belt;
a second timing belt; and
a transmission mechanism between said first timing belt and said second timing belt, wherein said scattered ray inhibition apparatus is mounted on said first timing belt, said radiation field control apparatus is mounted on said second timing belt, the transmission ratio of said transmission mechanism is equal to the ratio of the moving speed of said scattered ray inhibition apparatus to the moving speed of said radiation field control apparatus.

16. The X-ray machine according to claim 15, wherein said transmission mechanism comprises at least two gears.

17. The X-ray machine according to claim 16, wherein said transmission mechanism further comprises:
a third timing belt connected to said first timing belt; and
a fourth timing belt connected to said second timing belt, wherein said at least two gears are disposed between said third timing belt and said fourth timing belt.

18. The X-ray machine according to claim 15 further comprising a first linear guideway, said scattered ray inhibition apparatus being connected to said first timing belt through said first linear guideway.

19. The X-ray machine according to claim 18 further comprising a second linear guideway, said radiation field control apparatus being connected to said second timing belt through said second linear guideway.

20. The X-ray machine according to claim 15 further comprising a second linear guideway, said radiation field control apparatus being connected to said second timing belt through said second linear guideway.

* * * * *